United States Patent
Gulachenski

(10) Patent No.: US 8,992,506 B2
(45) Date of Patent: Mar. 31, 2015

(54) MICROCATHETER

(75) Inventor: Joseph Gulachenski, Trabuco Canyon, CA (US)

(73) Assignee: MircoVention, Inc., Tustin, CA (US)

( * ) Notice: Subject to any disclaimer, the term of this patent is extended or adjusted under 35 U.S.C. 154(b) by 987 days.

(21) Appl. No.: 12/635,465

(22) Filed: Dec. 10, 2009

(65) Prior Publication Data

US 2010/0160899 A1 Jun. 24, 2010

Related U.S. Application Data

(60) Provisional application No. 61/121,525, filed on Dec. 10, 2008.

(51) Int. Cl.
*A61M 25/00* (2006.01)

(52) U.S. Cl.
CPC ......... *A61M 25/0009* (2013.01); *A61M 25/005* (2013.01); *A61M 25/0053* (2013.01); *A61M 25/0054* (2013.01); *A61M 2025/0042* (2013.01)
USPC ....................................................... 604/525

(58) Field of Classification Search
CPC ................. A61M 2025/0042; A61M 25/0009; A61M 25/005; A61M 25/0053; A61M 25/0054
USPC ........ 604/525, 524, 523, 93.01, 95.01–95.05, 604/264
See application file for complete search history.

(56) References Cited

U.S. PATENT DOCUMENTS

| | | | |
|---|---|---|---|
| 3,225,762 A | 12/1965 | Guttman | |
| 3,537,451 A | 11/1970 | Murray et al. | |
| 3,559,643 A | 2/1971 | Pannier, Jr. et al. | |
| 3,570,485 A | 3/1971 | Reilly | |
| 3,742,958 A | 7/1973 | Rundles | |
| 3,769,975 A | 11/1973 | Nimoy et al. | |
| 3,815,608 A | 6/1974 | Spinosa et al. | |
| 3,853,130 A | 12/1974 | Sheridan | |
| 3,877,429 A | 4/1975 | Rasumoff | |
| 4,306,562 A | 12/1981 | Osborne | |
| 4,402,685 A | 9/1983 | Bühler et al. | |
| 4,412,832 A | 11/1983 | Kling et al. | |
| 4,449,973 A | 5/1984 | Luther | |
| 4,663,358 A | 5/1987 | Hyon et al. | |
| 4,709,698 A | 12/1987 | Johnston et al. | |
| 4,739,768 A | 4/1988 | Engelson | |

(Continued)

FOREIGN PATENT DOCUMENTS

WO WO 00/69502 A1 11/2000
WO WO 2004/033015 A1 4/2004

OTHER PUBLICATIONS

United States Patent and Trademark Office, Final Office Action mailed Dec. 6, 2012 in U.S. Appl. No. 12/635,465, 13 pages.

(Continued)

*Primary Examiner* — Nicholas Lucchesi
*Assistant Examiner* — Diva K Chander
(74) *Attorney, Agent, or Firm* — Inskeep IP Group, Inc.

(57) ABSTRACT

A microcatheter comprises a coil formed over an inner liner. The coil is covered with a series of outer jacket segments that decrease in durometer relative to proximally adjacent segments. Preferably, these segments have angled ends that allow each segment to be inserted and bonded into the segment prior to it. The outer jacket ultimately terminates at a distal of the microcatheter with the segment having the lowest durometer.

19 Claims, 6 Drawing Sheets

(56) References Cited

U.S. PATENT DOCUMENTS

| | | | |
|---|---|---|---|
| 4,808,155 A | 2/1989 | Mahurkar | |
| 4,840,613 A | 6/1989 | Balbierz | |
| 4,853,130 A | 8/1989 | D'Angelo et al. | |
| 4,884,579 A | 12/1989 | Engelson | |
| 4,887,997 A | 12/1989 | Okada | |
| 4,932,946 A | 6/1990 | Shields | |
| 4,988,356 A | 1/1991 | Crittenden et al. | |
| 5,011,488 A | 4/1991 | Ginsburg | |
| 5,234,411 A | 8/1993 | Vaillancourt | |
| 5,250,033 A | 10/1993 | Evans et al. | |
| 5,258,042 A | 11/1993 | Mehta | |
| 5,279,590 A | 1/1994 | Sinko et al. | |
| 5,413,791 A | 5/1995 | Rhee et al. | |
| 5,489,273 A | 2/1996 | Whitney et al. | |
| 5,509,910 A * | 4/1996 | Lunn | 604/525 |
| 5,570,585 A | 11/1996 | Vaynberg | |
| 5,662,622 A * | 9/1997 | Gore et al. | 604/526 |
| 5,693,085 A * | 12/1997 | Buirge et al. | 623/1.13 |
| 5,702,373 A * | 12/1997 | Samson | 604/527 |
| 5,711,909 A * | 1/1998 | Gore et al. | 264/320 |
| 5,733,400 A * | 3/1998 | Gore et al. | 156/158 |
| 5,772,641 A | 6/1998 | Wilson | |
| 5,889,890 A | 3/1999 | Heimburger | |
| 5,895,378 A | 4/1999 | Nita | |
| 5,906,605 A * | 5/1999 | Coxum | 604/525 |
| 5,928,260 A | 7/1999 | Chin et al. | |
| 5,971,975 A * | 10/1999 | Mills et al. | 604/527 |
| 6,015,424 A | 1/2000 | Rosenbluth et al. | |
| 6,042,578 A * | 3/2000 | Dinh et al. | 604/527 |
| 6,152,912 A * | 11/2000 | Jansen et al. | 604/526 |
| 6,159,197 A | 12/2000 | Heuser | |
| 6,165,193 A | 12/2000 | Greene, Jr. et al. | |
| 6,186,978 B1 | 2/2001 | Samson et al. | |
| 6,193,691 B1 | 2/2001 | Beardsley | |
| 6,210,396 B1 * | 4/2001 | MacDonald et al. | 604/529 |
| 6,296,631 B2 | 10/2001 | Chow | |
| 6,299,619 B1 | 10/2001 | Greene, Jr. et al. | |
| 6,361,528 B1 | 3/2002 | Wilson et al. | |
| 6,447,540 B1 | 9/2002 | Fontaine et al. | |
| 6,500,190 B2 | 12/2002 | Greene, Jr. et al. | |
| 6,503,353 B1 * | 1/2003 | Peterson et al. | 156/86 |
| 6,524,274 B1 | 2/2003 | Rosenthal et al. | |
| 6,623,450 B1 | 9/2003 | Dutta | |
| 6,656,214 B1 | 12/2003 | Fogarty et al. | |
| 6,695,811 B2 | 2/2004 | Samson et al. | |
| 6,723,108 B1 | 4/2004 | Jones et al. | |
| 7,066,904 B2 | 6/2006 | Rosenthal et al. | |
| 7,229,454 B2 | 6/2007 | Tran et al. | |
| 7,695,488 B2 | 4/2010 | Berenstein et al. | |
| 2002/0156459 A1 | 10/2002 | Ye et al. | |
| 2003/0055374 A1 | 3/2003 | Martins et al. | |
| 2003/0195490 A1 | 10/2003 | Boatman et al. | |
| 2004/0103516 A1 * | 6/2004 | Bolduc et al. | 29/446 |
| 2004/0138625 A1 | 7/2004 | Flodin | |
| 2004/0243102 A1 * | 12/2004 | Berg et al. | 604/525 |
| 2005/0049574 A1 * | 3/2005 | Petrick et al. | 604/525 |
| 2005/0245897 A1 * | 11/2005 | Bolduc et al. | 604/524 |
| 2006/0052750 A1 * | 3/2006 | Lenker et al. | 604/164.01 |
| 2006/0106421 A1 | 5/2006 | Teoh | |
| 2006/0116636 A1 | 6/2006 | Murphy et al. | |
| 2006/0155302 A1 * | 7/2006 | Sisken et al. | 606/108 |
| 2006/0264905 A1 | 11/2006 | Eskridge et al. | |
| 2007/0100285 A1 * | 5/2007 | Griffin et al. | 604/164.11 |
| 2007/0135734 A1 | 6/2007 | Reynolds et al. | |
| 2008/0167628 A1 | 7/2008 | Li et al. | |
| 2008/0200874 A1 * | 8/2008 | Ferry | 604/103.1 |
| 2008/0228171 A1 * | 9/2008 | Kugler et al. | 604/529 |
| 2010/0057018 A1 * | 3/2010 | Lentz et al. | 604/264 |
| 2010/0160899 A1 * | 6/2010 | Gulachenski | 604/525 |

OTHER PUBLICATIONS

United States Patent and Trademark Office, Office Action mailed Sep. 5, 2012 in U.S. Appl. No. 12/188,581, 14 pages.

United States Patent and Trademark Office, Office Action mailed Jun. 12, 2012 in U.S. Appl. No. 12/635,465, 9 pages.

European Patent Office, Extended European Search Report dated Apr. 19, 2012 in European Patent Application No. EP09832559, 7 pages.

WIPO, U.S. International Preliminary Examining Authority, International Preliminary Report on Patentability mailed Jun. 23, 2011 in International Patent Application No. PCT/US2009/067554, 7 pages.

United States Patent and Trademark Office, Final Office Action mailed Jan. 20, 2011 in U.S. Appl. No. 12/188,581, 17 pages.

United States Patent and Trademark Office, Office Action mailed Jun. 28, 2010 in U.S. Appl. No. 12/188,581, 13 pages.

WIPO, U.S. International Search Authority, International Search Report and Written Opinion mailed Feb. 3, 2010 in International Patent Application No. PCT/US2009/067554, 8 pages.

United States Patent and Trademark Office, Office Action mailed Oct. 2, 2009 in U.S. Appl. No. 12/188,581, 15 pages.

United States Patent and Trademark Office, Final Office Action mailed Jul. 11, 2007 in U.S. Appl. No. 10/755,249, 17 pages.

United States Patent and Trademark Office, Office Action mailed Dec. 1, 2006 in U.S. Appl. No. 10/755,249, 10 pages.

* cited by examiner

| 150 | 152 | 154 | 156 | 158 | 160 | 162 |
|---|---|---|---|---|---|---|

Figure 3

| 164 | 166 | 168 | 170 | 172 | 174 | 176 |
|---|---|---|---|---|---|---|

Figure 4

MICROCATHETER

This application claims priority to U.S. Provisional Application Ser. No. 61/121,525 filed Dec. 10, 2008 entitled Microcatheter, the contents of which are incorporated in their entirety herein.

FIELD OF THE INVENTION

The present invention relates generally to medical devices and methods of manufacturing the same. More particularly, this invention relates to microcatheters and methods for making microcatheters used in performing endovascular medical procedures.

BACKGROUND OF THE INVENTION

Microcatheters are used in a variety of medical procedures for the diagnosis and treatment of conditions and diseases occurring in remote, highly tortuous vascular sites. Typically, a microcatheter is introduced to the vascular system of a patient at a first location and then is advanced through the patient's vessels until the distal end of the microcatheter reaches a desired target location.

The process of advancing the microcatheter often involves applying force proximal of its distal end. Hence, as some prior art microcatheters advance deeper into the vascular system, it can become difficult to properly push and maneuver the distal end of the microcatheter. In this respect, it is desirable that a microcatheter exhibit superior pushability and trackability. Pushability is often understood as the ability to transmit force from the proximal end of the microcatheter to the distal end of the microcatheter while minimizing or eliminating kinking. Trackability is often understood as the ability to navigate the microcatheter through tortuous vasculature.

While prior art microcatheters are typically capable of performing their intended task within a patient, it is always desirable to have improved catheter performance, such as improved trackability and pushability.

SUMMARY OF THE INVENTION

In one preferred embodiment according to the present invention, a microcatheter comprises a coil formed over an inner liner. The coil is covered with a series of outer jacket segments or transition segments that decrease in durometer relative to proximally adjacent segments. Preferably, these segments have angled ends that allow each segment to be inserted and bonded into the segment prior to it. The outer jacket ultimately terminates at a distal of the microcatheter with the segment having the lowest durometer.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 3 illustrates different example segments forming the outer jacket of the microcatheter according to a preferred embodiment of the present invention;

FIG. 4 illustrates different example segments forming the outer jacket of the microcatheter according to a preferred embodiment of the present invention;

DESCRIPTION OF EMBODIMENTS

Figure 1A:
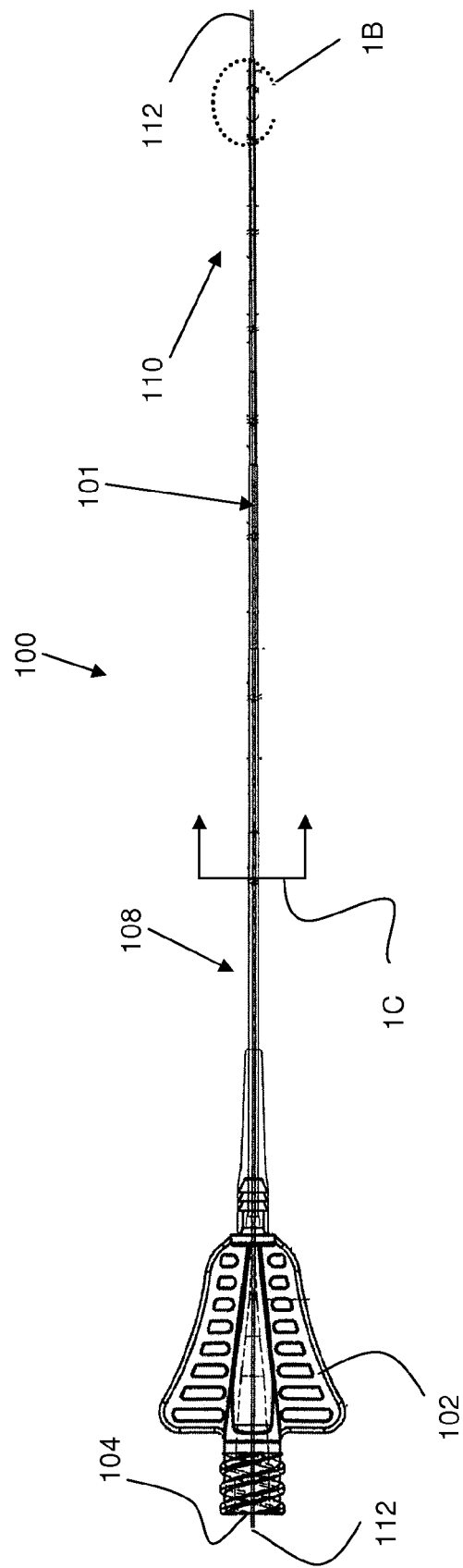
FIG. 1A illustrates a side cross sectional view of a microcatheter according to a preferred embodiment of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

FIG. 1A illustrates a preferred embodiment of a microcatheter 100 comprising an elongated tubular member 101 connected to a hub member 102. The proximal end 108 of the tubular member 101 is coupled to a distal end of the hub 102 and is further covered by a strain relief member 106. At least one center lumen in the tubular member 101 is in communication with a passage within the hub 102, thereby forming catheter passage 104. In the present example embodiment, a guide wire 112 is positioned through passage 104, exiting at a distal end 110 of the tubular member.

The hub 102 is preferably bonded to the proximal portion 108 with DYMAX medical adhesion or a similar adhesive. The strain relief portion 106 may be installed onto the hub 102 by friction, adhesive or similar connection techniques.

Figure 1B:
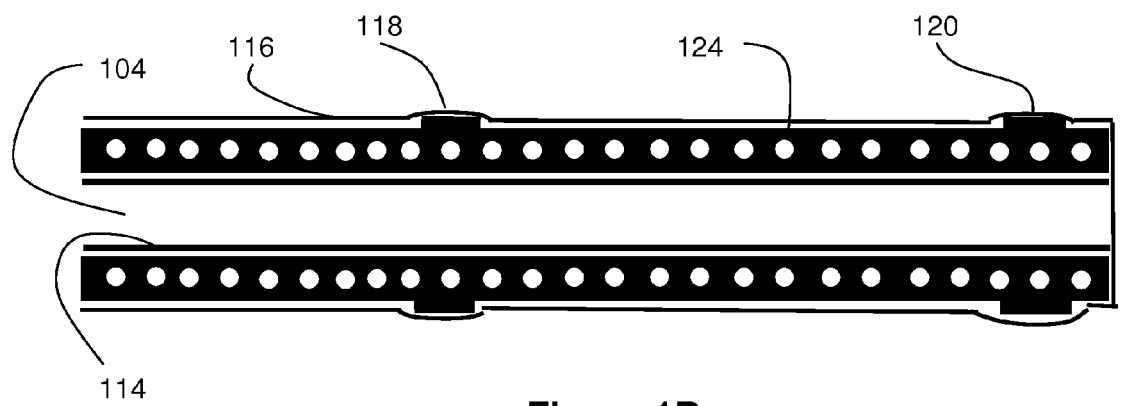
FIG. 1B illustrates a magnified view of a distal region of the microcatheter of FIG. 1A taken from area 1B.
Figure 1C:
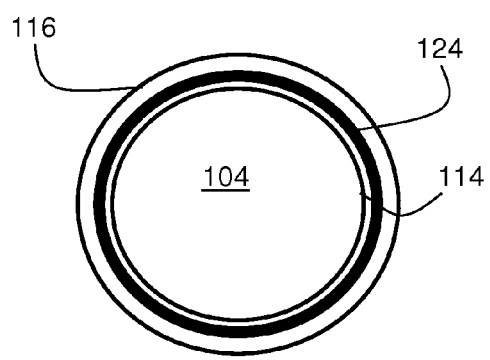
FIG. 1C illustrates a cross sectional view of the microcatheter of FIG. 1A taken along lines 1C.

As best seen in FIGS. 1B and 1C, the passage 104 is formed by an inner liner 114 about which is wound a coil 124. The coil 124 is covered by an outer jacket 116 that is formed from a plurality different section. Each section of the outer jacket 116 preferably has a durometer that is less that the section proximal to it. In this respect, the outer jacket 116 generally increases in flexibility towards the distal end 110 relative to the proximal end 108.

Figure 2A:
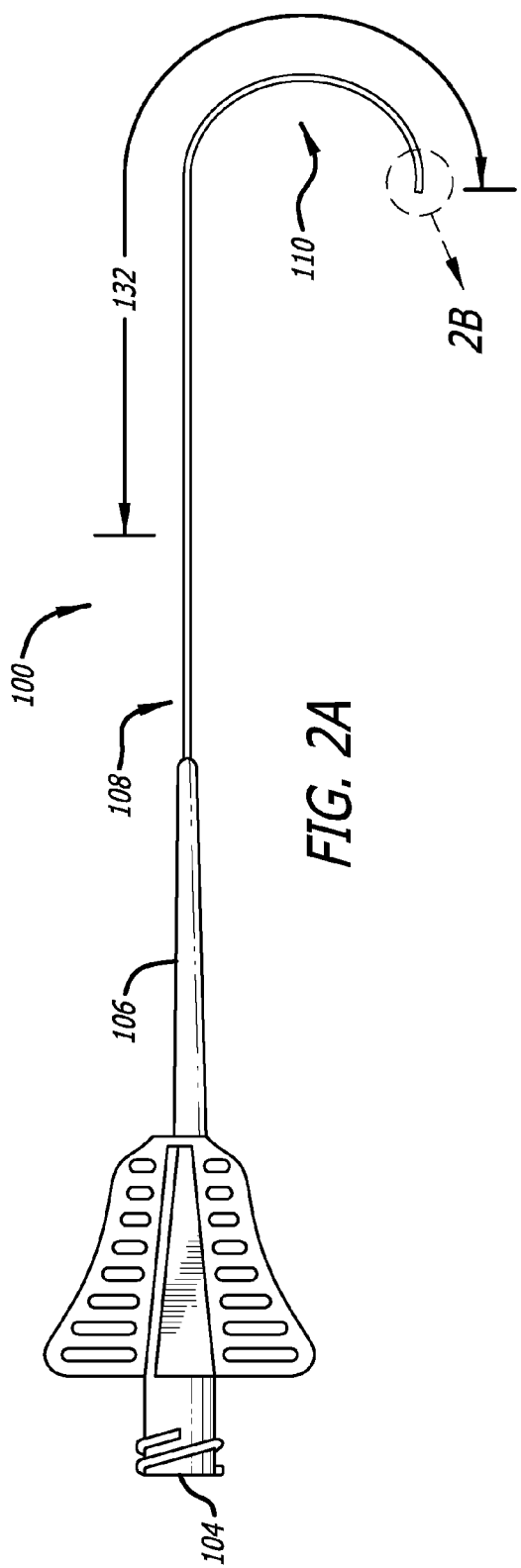
FIG. 2A illustrates the microcatheter of FIG. 1A having a curved distal region.

As seen in FIG. 2A, the outer jacket preferably includes a hydrophilic coating along a portion of its length. Preferably, this coating is about 100-120 cm from the distal tip of the microcatheter 100.

Figure 2B:
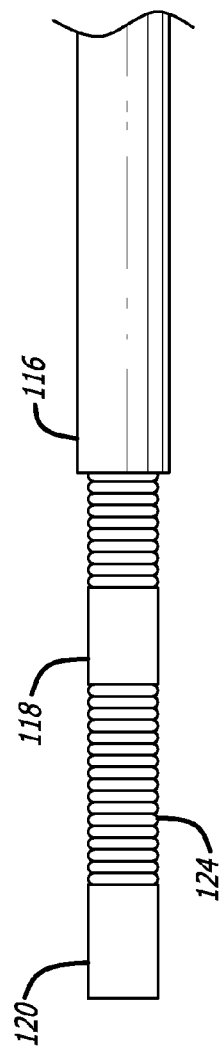
FIG. 2B illustrates a distal region of the microcatheter from area 2B with the outer jacket partially removed.

As seen in the cross sectional view of FIG. 1B and the view of FIG. 2B, the distal end 110 includes two radiopaque markers 118 and 120 that are bonded between the coil layer 124 and the outer jacket 116. In one example arrangement, the marker 120 is located at or near the distal tip of the catheter 100, while the marker 118 is located about 3 cm proximal of marker band 120. As best seen in FIG. 1B, these markers 118 and 120 can provide raised or elevated areas that can be used to secure an implant device such as a stent.

In one example, the microcatheter 100 is approximately 150 cm, as measured from the distal tip of the strain relief portion 106 to the distal end of the distal portion 110. The central lumen 104 has an inner diameter of approximately 0.0165 to 0.017 inches. The distal portion 110 preferably includes a region approximately 40 cm long that is approximately 1.9 French. The proximal portion 108 preferably includes a region of approximately 2.4 French. The outer jacket 116 is about 0.025 inches.

The inner liner 114 is preferably composed of polytetrafluroethelyene, PTFE, or other similar material and has a wall thickness in the range of about 0.0005 and 0.007 inches. Preferably, the inner liner 114 is "necked" or stretched to reduce wall thickness. This stretching can also selectively orient the molecular structure of the material and thereby impart additional performance characteristics. For example, such stretching can increase burst strength and/or increase compliance or suppleness as compared with similar, non-stretched material of the same thickness.

In this respect, a smaller portion of the microcatheter 100 is used for the inner liner 114 while the thickness of other portions can be increased without increasing the outer diameter or reducing the inner diameter of the microcatheter 100. In other words, stretching the inner liner 114 allows a different thickness ratio between the inner liner 114 and other portions of the microcatheter, such as the outer jacket 116.

For example, in a 10 system microcatheter having an inner lumen diameter in the range of about 0.0165 to 0.017 inches and an outer diameter of about 0.025 inches, there is a ratio of outer jacket 116 thickness to inner liner 114 thickness greater than about 70% and more preferably about 78% while achieving desirable performance results.

Preferably, the inner liner 114 is stretched prior to assembly by applying heat and tension to the liner 114. For example, a temperature between about 250° F. and 600° F. can be applied to the liner 114 while a tension between about 50 g to 750 g at a speed between 0.5 and 12 inches per minute. In another example, the inner liner 114 can be stretched at room temperature with similar or stronger forces and similar or quicker speeds.

In one preferred embodiment, the inner liner 114 can have a uniform thickness along its length. In another preferred embodiment, the inner liner 114 can increase in thickness towards its proximal end, thereby imparting additional burst strength.

The coil layer 124 is preferably formed of a round wire with an outer diameter of approximately 0.001 inch filar. The pitch of coil 124 is preferably in the range of about 0.002 to 0.004 inches. In certain embodiments of the microcatheter 100, coil 124 may also be formed with a tighter pitch.

In one example, the outer jacket 116 is formed of a plurality of segments of polyether block amide, Pebax, of varying durometer bonded to one another (e.g., heat bonded or adhesive bonding). As illustrated in FIG. 5C, a first jacket segment 116A includes a biased or angled end 116D. In other words, the segment end 116D is nonperpendicular to an axis 116E along the length of the segment 116A. Preferably, this angle can be within a range of about 5-75 degrees relative to the axis 116E.

Figure 5A:
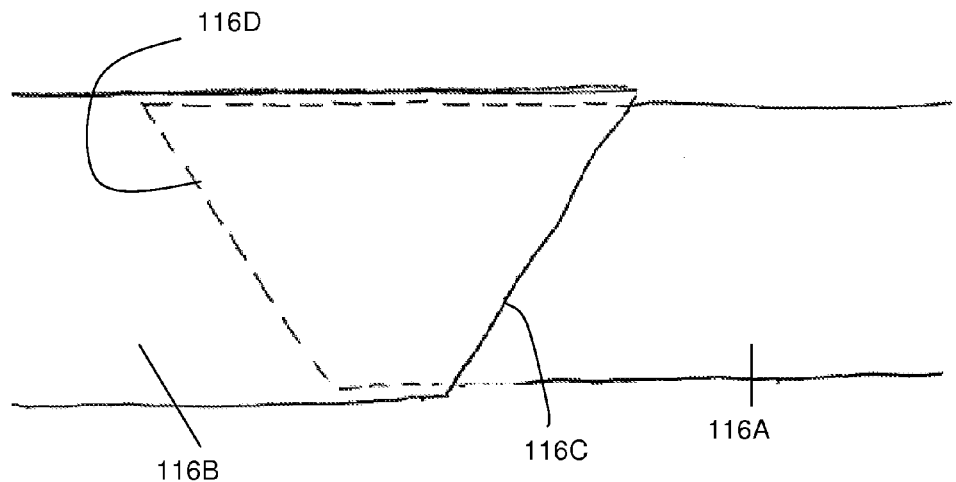
FIG. 5A illustrates a side view of two outer jacket segments with opposing or oppositely oriented diagonal angled ends.

As seen in FIG. 5A, segment 116A is angle-bonded within jacket segment 116B. The angled cut end 116D is oriented such that it is in an opposite rotational position relative to the angled cut end 116C. In other words, the angles of ends 116D and 116C are positioned so as to form a triangular or trapezoid shape.

Preferably, segments 116A and 116B are bonded by first placing the angled cut end 116D against angled cut end 116C. Next, a heat shrink tube is positioned over the two segments 116A and 116B. Finally, heat is applied, causing the heat shrink tube to shrink in diameter, pushing segment 116A within segment 116B. Both the heat and the force of the heat shrink tube cause the segments 116A and 116B to bond together. Finally, the heat shrink tube can be removed from the jacket segments.

Figure 5B:
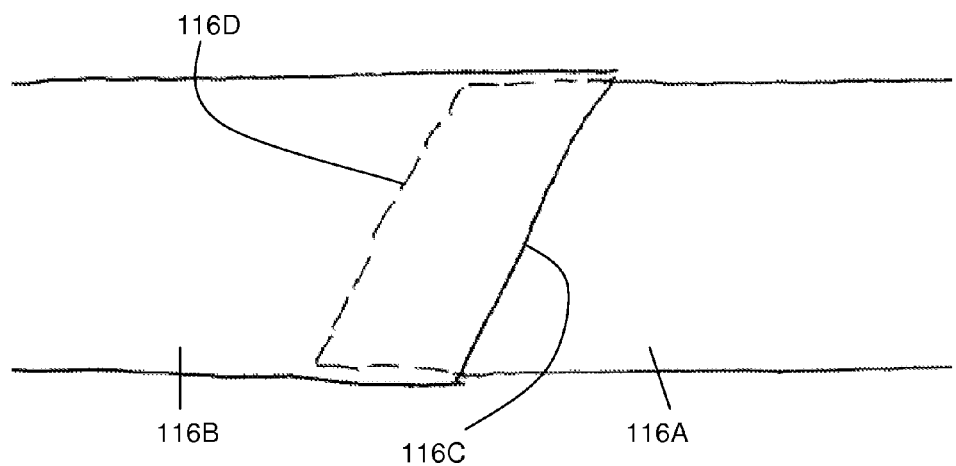
FIG. 5B illustrates a side view of two outer jacket segments with similarly oriented diagonal angled ends; and, FIG. 5C illustrates a side perspective view of a jacket segment with a diagonal angled end region.
Figure 5C:
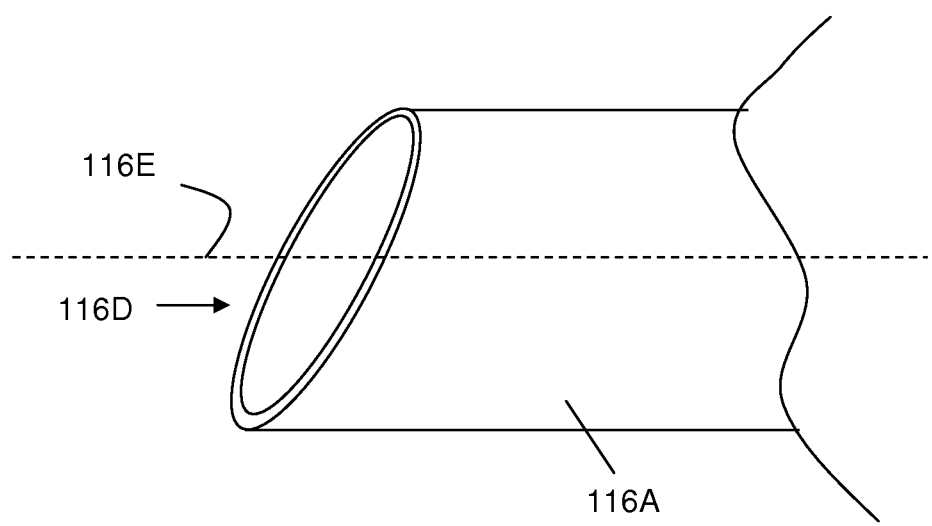

As illustrated in FIG. 5B, segment 116A may also be oriented such that the angled cut end 116D is positioned in the same direction and orientation as angled end 116C. While both segments are shown having angled ends, it is also contemplated that only a single segment may include an angled or biased end. The angled bonding as described in the examples of FIGS. 5A and 5B can reduce kinking that may otherwise occur by providing additional axial strength while maintaining flexibility.

Preferably, the outer jacket 116 has seven segments, each of which having a lower durometer than the segment proximally adjacent to it. In this respect, the outer jacket 116 becomes more flexible towards the distal end 110.

Turning to FIG. 3, an example outer jacket 116 is shown having various segments. Segment 150 represents a segment on the proximal end 108 while segment 162 represents a segment on the distal end 110. In one example, the segments are composed as follows:

| Jacket Segment Number | Material | Length (approximate) | Internal Diameter (approximate) | Outer Diameter (approximate) |
| --- | --- | --- | --- | --- |
| 150 | Grilamid L25 | 85 cm | 0.026 inches | 0.035 inches |
| 152 | Pebax 72 | 5 cm | 0.026 inches | 0.035 inches |
| 154 | Pebax 63D1 | 5 cm | 0.026 inches | 0.033 inches |
| 156 | Pebax 55D1 | 5 cm | 0.026 inches | 0.032 inches |
| 158 | Pebax 45D2 | 20 cm | 0.026 inches | 0.031 inches |
| 160 | Pebax 45D1 | 15 cm | 0.026 inches | 0.030 inches |
| 162 | Pebax 35D | 15 cm | 0.026 inches | 0.029 inches |

Turning to FIG. 4, an example outer jacket 116 is shown having various segments. Segment 164 represents a segment on the proximal end 108 while segment 176 represents a segment on the distal end 110. In one example, the segments are composed as follows:

| Jacket Segment Number | Material | Length (approximate) | Internal Diameter (approximate) | Outer Diameter (approximate) |
|---|---|---|---|---|
| 164 | Grilamid L25 | 84 cm | 0.026 inches | 0.035 inches |
| 166 | Pebax 72D | 5 cm | 0.026 inches | 0.034 inches |
| 168 | Pebax 63D1 | 5 cm | 0.026 inches | 0.033 inches |
| 170 | Pebax 55D1 | 35 cm | 0.026 inches | 0.032 inches |
| 172 | Pebax 45D2 | 10 cm | 0.026 inches | 0.031 inches |
| 174 | Pebax 45D1 | 15 cm | 0.026 inches | 0.030 inches |
| 176 | Pebax 35D | 1 cm | 0.026 inches | 0.029 inches |

It will be recognized that suitable alternatives to Pebax and Grilamid are known in the field and may be employed accordingly. It will further be recognized that the wall thickness of the inner liner 114 and the outer jacket 116 may be altered so as to emphasize or enhance certain characteristics, such as the trackability, pushability, internal diameter, and/or outer diameter, of the microcatheter 100 as desired in order to perform the intended procedure.

Certain embodiments of the present invention provide for superior tip-shapeability and enhanced tip-shape retention in the microcatheter 100. With respect to tip-shapeability, the microcatheter 100 is formed in a straight, i.e. not pre-shaped, configuration that can be steam-shaped as desired by a physician prior to use. The catheter 100 can be steam-shaped in a manner well known in the field. The tip-shape retention of the microcatheter 100 is greater that 55 percent. In a preferred embodiment the tip-shape retention is 58 percent and in another preferred embodiment the tip-shape retention is 67 percent.

Tip-shape retention is enhanced by employing a thinner inner liner 114 which, in turn, allows for incorporation of a thicker walled, shapeable, outer jacket 116. Tip-shape retention is further enhanced by incorporating the coil 124 having a tight pitch between the inner liner 114 and the shapeable outer jacket 116. The tight pitch coil 124 is disposed concentrically about the inner liner 114 such that the shapeable section of the microcatheter 100, i.e. the distal portion 110, is not significantly subjected to a straightening force by the coil 124. This is in contrast to prior art microcatheters that employ a braided or a longer pitch coil configuration that disposes wire or other filaments in the shapeable section of the microcatheter in a manner that exert a straightening force to the microcatheter tip.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A microcatheter comprising:
an elongated tube having a plurality of segments;
each of said plurality of segments further comprising biased ends, wherein said biased ends are pushed into and bonded with adjacent segments;
each of said segments having a durometer that is lower than a proximally adjacent segment;
a coil located beneath said elongated tube and having a pitch within a range of about 0.002 to 0.004 inches; and,
an inner liner tube disposed beneath said coil, said inner liner tube being stretched to selectively orient a molecular structure of its material.

2. The microcatheter of claim 1, wherein said inner liner tube is stretched.

3. The microcatheter of claim 1, further comprising a hydrophilic coating disposed over said elongated tube between about 100-120 cm from a distal end of said elongated tube.

4. The microcatheter of claim 1, wherein each of said plurality of segments are angle-bonded to each other.

5. The microcatheter of claim 1, wherein said inner liner is composed of PTFE having a thickness in the range of about 0.0005 to about 0.007 inches.

6. A microcatheter sized for accessing a vasculature of a patient, comprising:
a first tube segment having a first axis along its length and a first angled end having a first nonperpendicular bias angle relative to said first axis; and
a second tube segment having a second end having a second non-perpendicular bias angle;
wherein said first angled end is disposed within said second tube segment and spaced apart from said second end, forming an elongated tube;
said elongated tube having a passage open near a distal and proximal end of said elongated tube.

7. The microcatheter of claim 6, wherein said second tube segment further comprises a second axis along its length and a second angled end having a second nonperpendicular angle relative to said second axis.

8. The microcatheter of claim 7, wherein said first nonperpendicular angle and said second nonperpendicular angle are positioned in an opposite orientation relative to each other.

9. The microcatheter of claim 7, wherein said first nonperpendicular angle and said second nonperpendicular angle are positioned in a matching orientation relative to each other.

10. The microcatheter of claim 7, wherein said elongated tube further comprises a plurality of tube segments at least partially disposed within at least one other of said plurality of tube segments; each of said plurality of tube segments comprising at least one angled end.

11. The microcatheter of claim 6, wherein said elongated tube further comprises a plurality of tube segments, each of which being composed of a material having a different durometer.

12. The microcatheter of claim 11, wherein said elongated tube is disposed over a coil having a pitch between about 0.002 and 0.004 inches.

13. A microcatheter comprising:
an elongated tubular jacket having a first thickness and comprising a plurality of segments having biased, angled ends that are pushed into and bonded within adjacent segments; and, an inner tubular liner having a second thickness and being disposed within said elongated tubular jacket; wherein said elongated tubular jacket has an outer diameter of about 0.025 inches; and, wherein the ratio between said first thickness and said second thickness is greater than 70%.

14. The microcatheter of claim 13, wherein said ratio between said first thickness and said second thickness is 78%.

15. The microcatheter of claim 13, further comprising a coiled wire disposed between said elongated tubular jacket and said inner tubular liner.

16. The microcatheter of claim 13, wherein said inner tubular liner comprises a material that has been stretched.

17. The microcatheter of claim 13, wherein said inner tubular liner comprises PTFE.

18. The microcatheter of claim 13, wherein said elongated tubular jacket is composed of a plurality of angle-bonded jacket segments.

19. The microcatheter of claim 13, wherein said inner tubular liner comprises a stretched PTFE material.

* * * * *